United States Patent [19]

Yokomori et al.

[11] Patent Number: 5,362,636
[45] Date of Patent: Nov. 8, 1994

[54] PROCESS FOR PRODUCING L-LYSINE BY FERMENTATION WITH A BACTERIA HAVING SELENALYSINE RESISTANCE

[75] Inventors: Manabu Yokomori; Takeshi Niwa; Kazuhiko Totsuka; Yoshio Kawahara; Shigeru Nakamori, all of Kawasaki; Nobuyoshi Esaki, Otsu; Kenji Soda, Uji, all of Japan

[73] Assignee: Ajinomoto Co., Inc., Tokyo, Japan

[21] Appl. No.: 793,950

[22] Filed: Oct. 22, 1991

[30] Foreign Application Priority Data

Oct. 29, 1990 [JP] Japan ................... 2-291441

[51] Int. Cl.⁵ .................... C12P 13/08; C12N 1/20
[52] U.S. Cl. ................ 435/115; 435/252.1; 435/840; 435/843
[58] Field of Search .............. 435/115, 252.1, 840, 435/843

[56] References Cited

U.S. PATENT DOCUMENTS

| 3,708,395 | 1/1973 | Nakayama et al. | 435/115 |
| 3,732,144 | 5/1973 | Nakayama et al. | 435/115 |
| 3,825,472 | 7/1974 | Kubota et al. | 435/115 |
| 4,066,501 | 1/1978 | Tosaka et al. | 435/115 |

FOREIGN PATENT DOCUMENTS

| 2497231 | 7/1982 | France | 435/115 |
| 0100289 | 9/1974 | Japan | 435/115 |
| 0063095 | 4/1982 | Japan | 435/115 |
| 0088094 | 5/1984 | Japan | 435/115 |
| 2042995 | 2/1990 | Japan | 435/115 |
| 2103617 | 2/1983 | United Kingdom | 435/115 |

OTHER PUBLICATIONS

Hirao, T. et al., "L-Lysine Production in Continuous Culture of An L-Lysine Hyperproducing Mutant of *Corynebacterium glutamicum*," *Appl. Microbiol. and Biotechnology* vol. 32, 1989, pp. 269-273.

Tosaka et al., "Lysine" In: Biotechnology and Amino Acid Production, Aida et al. (eds); vol. 24; Elsevier; 1986; pp. 152-172.

Chemical Abstracts, vol. 102, No. 1, Jan. 7, 1985, No. 59035T, E. Shimizu, et al., "Effect of a Selenium Analog of L-Lysine On Lysine Transport of Candida Pelliculosa".

Chemical Abstracts, vol. 101, No. 1, Jul. 2, 1984, No. 51438K, V. Busiello, et al., "Effects of Thialysine and Selenalysine On Lysine Biosynthesis".

Chemical Abstracts, vol. 103, No. 1, Jul. 8, 1985, No. 3377J, M. Di Girolamo, et al., "Effects of Selenalysine On Lysine Biosynthesis".

*Primary Examiner*—Marian Knode
*Attorney, Agent, or Firm*—Oblon, Spivak, McClelland, Maier & Neustadt

[57] ABSTRACT

A process for producing L-lysine, which comprises culturing a mutant L-lysine-producing strain belonging to the genus Brevibacterium or the genus Corynebacterium and having selenalysine resistance in a nutrient medium, producing and accumulating L-lysine in the culture broth and collecting L-lysine from the culture broth.

9 Claims, No Drawings

PROCESS FOR PRODUCING L-LYSINE BY FERMENTATION WITH A BACTERIA HAVING SELENALYSINE RESISTANCE

BACKGROUND OF THE INVENTION

1. Field of the Invention

The present invention relates to a process for producing L-lysine by fermentation.

2. Description of the Background

L-lysine is one of the essential amino acids. It is the first limiting amino acid of cereals and is an important amino acid used in assorted feed for broilers or swine.

In conventional processes for producing L-lysine, artificial variants of microorganisms isolated and derived from the natural world have been used. It is known that most of these artificial variants are derived from microorganisms belonging to the genus Brevibacterium or the genus Corynebacterium. It is also known that the biosynthesis system of L-lysine has been potentiated by imparting to the microorganisms properties such as auxotrophy, resistance as well as sensitivity to amino acid analogs, chemical drugs and the like in combination or adding these properties successively ("AMINO SAN HAKKO (Amino Acid Fermentation)", edited by H. Aida, K. Takinami, I. Chibata, K. Nakayama and H. Yamada; Gakkai Shuppan Center, 1986, page 273.

However, the conventional processes are quite expensive and relatively inefficient. Thus, a need exists for a process for producing L-lysine which is less expensive and which has an improved efficiency.

SUMMARY OF THE INVENTION

Accordingly, it is an object of the present invention to provide a process for producing L-lysine which is less expensive than conventional processes.

It is also an object of this invention to provide a process for producing L-lysine which is more efficient than conventional processes.

The above objects and others are provided by a process for producing L-lysine, which entails culturing a mutant L-lysine-producing strain belonging to the genus Brevibacterium or the genus Corynebacterium and having selenalysine resistance in a nutrient medium, producing and accumulating L-lysine in the culture broth and collecting L-lysine from the culture broth.

DETAILED DESCRIPTION OF THE PREFERRED EMBODIMENTS

In accordance with the present invention, a method is provided for producing L-lysine by fermentation in a manner which is, at once, relatively inexpensive and efficient as compared to conventional processes for producing L-lysine.

The present inventors have made extensive investigations to acquire variants having improved L-lysine productivity from microorganisms belonging to the genus Brevibacterium or the genus Corynebacterium. As a result, it has been surprisingly discovered that mutant strains having improved L-lysine productivity can be obtained with high frequency in the variants to which selenalysine resistance has been imparted. The present invention has been accomplished based upon this discovery. Thus, the present invention provides a process for producing L-lysine which comprises culturing mutant L-lysine-producing strain belonging to the genus Brevibacterium or the genus Corynebacterium and having selenalysine resistance in a nutrient medium, producing and accumulating L-lysine in the culture broth and collecting L-lysine from the culture broth.

The selenalysine (hereafter abbreviated as Selys) referred to in the present invention has a chemical structure similar to lysine, wherein the methylene group at the $\gamma$-position of lysine is substituted with selenium (Se).

As parent strains of the variants derived therefrom in the present invention (hereafter abbreviated as parent strains), any bacteria can be used irrespective of its species and strain so long as they belong to the genus Brevibacterium or the genus Corynebacterium.

For example, the following microorganisms known to be so called L-glutaminic acid-producing bacteria of Coryneform are employed.

*Brevibacterium divaricatum* ATCC 14020
*Brevibacterium flavum* ATCC 14067
*Brevibacterium lactofermentum* ATCC 13869
*Brevibacterium roseum* ATCC 13825
*Corynebacterium acetoacidophilum* ATCC 13870
*Corynebacterium lilium* ATCC 15990
*Corynebacterium glutamicum* ATCC 13032

In addition, there may also be used L-lysine-producing strains which are obtained by imparting properties such as L-alanine auxotrophy, and fluoropyruvate sensitivity, for example, which are already known to be effective for improving L-lysine productivity, to the microorganism described above.

The Selys resistance referred to in the present invention is used to mean the property of such a variant that can grow in a medium containing Selys of a concentration which inhibits the growth of the parent strain.

The variants used in the present invention can be easily obtained by subjecting the parent strains described above to a mutation inducing treatment, e.g., UV irradiation, or a treatment with chemicals such as N-methyl-N'-nitro-N-nitrosoguanidine (hereafter referred to as NG) or nitric acid, and then collecting the variants which can grow in a medium containing Selys of such a concentration, e.g., 500 $\mu$g/ml, that inhibits the growth of the parent strain.

Specific examples of the variants which can be used in the present invention include the following strains.

*Brevibacterium lactofermentum* AJ 12564, FERM BP- 3554 (Selys$^\gamma$)
*Corynebacterium acetoacidophilum* AJ 12565, FERM BP- 3555 (Selys$^\gamma$)
*Brevibacterium lactofermentum* AJ 12566, FERM BP- 3556 (AEC$^\gamma$, Ala$^-$, Selys$^\gamma$)
*Brevibacterium flavum* AJ 12568, FERM BP- 3557 (AEC$^\gamma$, PK$^w$, Selys$^\gamma$)
*Corynebacterium glutamicum* AJ 12579, FERM BP- 3559 (AEC$^\gamma$, Selys$^\gamma$)

Symbols within parentheses are used to mean:
Selys$^\gamma$: selenalysine resistance
AEC$_\gamma$: S-(2-aminoethyl)-L-cysteine resistance
Ala$^-$: alanine auxotrophy
PK$^w$: reduced pyruvate kinase activity The variants described above were deposited on Oct. 25, 1990 in the Fermentation Research Institute, Agency of Industrial Science and Technology, Ministry of International Trade and Industry (FRI) located at 1-3, Higashi 1-chome, Tsukuba-shi, Ibaraki-ken 305, Japan and then transferred to a deposit on Sep. 10, 1991 pursuant to the Budapest Treaty.

As the carbon sources in the nutrient medium which is used for culturing the present mutant strain, there can be used sugars such as glucose, and molasses, for example; organic acids such as acetic acid, and citric acid, for example, and; alcohols such as ethanol, for example.

As the nitrogen sources, there can be used ammonium sulfate, ammonium nitrate, ammonium chloride, ammonium phosphate, urea, ammonia water, and ammonia gas, and other conventional nitrogen sources.

As the organic nutrients, there may be used soybean protein acid hydrolysate, and yeast extract, for example.

Conditions for culturing the present mutant strain preferably aerobic at a fermentation temperature of about 30 to 35° C. for a fermentation period of about 40 to 100 hours. It is preferred to maintain pH in the range of about 6.5 to 7.0 at the initial stage and during the fermentation. For adjusting pH, conventional agents, such as inorganic or organic acidic or alkaline substances, and furthermore, urea, calcium carbonate, or ammonia gas, for example, may be used.

Collection of L-lysine from the fermentation broth may be performed generally by the ion exchange resin method and other known techniques in combination.

The present invention will now be further described by reference to certain examples which are provided solely for illustration and are not intended to be limitative.

EXAMPLE 1

*Brevibacterium lactofermentum* ATCC 13869 was cultured in a medium containing 1% peptone, 1% yeast extract, 0.5% NaCl and 0.5% glucose, pH being adjusted to 7.0. After collecting the cells, a treatment was carried out with 0.1M phosphate buffer (pH 7.0) containing 250 μg/ml of NG at 30° C. for 30 minutes. Then, the cells having a survival rate of 1.0% were inoculated on agar plate minimum medium containing 500 μg/ml of Selys (Table 1) and cultured at 30° C. for 7 days. *Brevibacterium lactofermentum* AJ 12564 (FERM BP-3554) was obtained from the colonies grown.

*Brevibacterium lactofermentum* ATCC 13869 which is the parent strain cannot grow (Selys-sensitive) on the aforesaid agar plate minimum medium containing 500 μg/ml of Selys, whereas the obtained variant, *Brevibacterium lactofermentum* AJ 12564 can grow on the medium (Selys resistant). By this difference, the variant used in the present invention can be clearly distinguished from the parent or other variants.

TABLE 1

| Composition of Minimum Medium | |
| --- | --- |
| Component | Concentration |
| Glucose | 20 g/l |
| Ammonium sulfate | 10 g/l |
| KH$_2$PO$_4$ | 1 g/l |
| MgSO$_4$.7H$_2$O | 0.4 g/l |
| FeSO$_4$.7H$_2$O | 10 mg/l |
| MnSO$_4$.4H$_2$O | 10 mg/l |
| Biotin | 50 μg/l |
| Thiamine hydrochloride | 100 μg/l |
| Urea | 2 g/l |
| | (pH 7.0) |

TABLE 2

| L-Lysine-Producing Medium | |
| --- | --- |
| Component | Concentration |
| Glucose | 100 g/l |
| Ammonium sulfate | 45 g/l |
| KH$_2$PO$_4$ | 1 g/l |
| MgSO$_4$.7H$_2$O | 0.4 g/l |
| FeSO$_4$.7H$_2$O | 10 mg/l |

TABLE 2-continued

| L-Lysine-Producing Medium | |
| --- | --- |
| Component | Concentration |
| MnSO$_4$.4H$_2$O | 10 mg/l |
| Biotin | 50 μg/l |
| Thiamine hydrochloride | 200 μg/l |
| Soybean protein hydrolysate concentrate (total nitrogen 7%) | 15 μg/l |
| | (pH 7.0) |

Next, upon production of L-lysine by fermentation, the L-lysine-producing medium shown in Table 2 was prepared and 20 ml each of the medium was separately charged in a shake flask of 500 ml volume. After sterilization with heating at 115° C. for 10 minutes, 1 g of calcium carbonate which had been previously subjected to dry air sterilization was added to the medium. *Brevibacterium lactofermentum* ATCC 13869 and AJ 12564 were inoculated, respectively, on the medium followed by culturing at 31.5° C. for 72 hours by a back-and-forth shaker. An amount of L-lysine (calculated as the L-lysine monohydrochloride) accumulated in the fermentation broth was quantitatively determined, and is shown in Table 3. With the Selys resistant mutant strain, a marked increase of L-lysine accumulation was noted as compared with the parent strain.

TABLE 3

| Strain | Sensitive or Resistant to Selys | Amount of L-Lysine HCl Accumulated (g/dl) |
| --- | --- | --- |
| ATCC 13869 | sensitive | 0.01 |
| AJ 12564 | resistant | 2.32 |

EXAMPLE 2

*Corynebacterium acetoacidophilum* ATCC 13870 was subjected to a mutation with NG treatment in a manner similar to Example 1 to give *Corynebacterium acetoacidophilum* AJ 12565 (FERM BP-3555) as a Selys resistant strain. *Corynebacterium acetoacidophilum* ATCC 13870 and AJ 12565 were cultured in the same manner as in Example 1 and L-lysine productivity was examined. The results are shown in Table 4.

TABLE 4

| Strain | Sensitive or Resistant to Selys | Amount of L-Lysine HCl Accumulated (g/dl) |
| --- | --- | --- |
| ATCC 13870 | sensitive | 0.01 |
| AJ 12565 | resistant | 2.21 |

EXAMPLE 3

S-(2-Aminoethyl)-L-cysteine-resistant and alanine auxotrophic *Brevibacterium lactofermentum* AJ 3424 (FERM P-1711) was subjected to a mutation treatment with NG in a manner similar to Example 1, to give *Brevibacterium lactofermentum* AJ 12566 (FERM BP-3556) as a Selys resistant strain. *Brevibacterium lactofermentum* AJ 3424 and AJ 12566 were cultured in the same manner as in Example 1 and L-lysine productivity was examined. The results are shown in Table 5. The production amount was improved by 20.3% with *Brevibacterium lactofermentum* AJ 12566, as compared with AJ 3445.

TABLE 5

| Strain | Sensitive or Resistant to Selys | Amount of L-Lysine HCl Accumulated (g/dl) |
| --- | --- | --- |
| ATCC 3424 | sensitive | 2.32 |
| AJ 12566 | resistant | 2.79 |

EXAMPLE 4

S-(2-Aminoethyl)-L-cysteine-resistant, lysine-producing Corynebacterium glutamicum AJ 3463; (FERM P-1987) was subjected to a mutation treatment in a manner similar to Example 1 to give Corynebacterium glutamicum AJ 12579 (FERM BP- 3559) as a Selys resistant strain Corynebacterium glutamicum AJ 3463 and AJ 12579 were cultured in the same manner as in Example 1 and L-lysine productivity was examined. The results are shown in Table 6.

TABLE 6

| Strain | Sensitive or Resistant to Selys | Amount of L-Lysine HCl Accumulated (g/dl) |
| --- | --- | --- |
| ATCC 3463 | sensitive | 2.21 |
| AJ 12579 | resistant | 2.64 |

EXAMPLE 5

S-(2-Aminoethyl)-L-cysteine-resistant Brevibacterium flavum ATCC 11841 (FERM P-6463), which pyruvate kinase activity had been reduced as compared to the wild strain, was subjected to a mutation treatment in a manner similar to Example 1 to give Brevibacterium flavum AJ 12568 (FERM BP- 3559) as a Selys resistant strain. Brevibacterium flavum AJ 11841 and ATCC 12568 were cultured in the same manner as in Example 1 and L-lysine productivity was examined. The results are shown in Table 7.

TABLE 7

| Strain | Sensitive or Resistant to Selys | Amount of L-Lysine HCl Accumulated (g/dl) |
| --- | --- | --- |
| ATCC 11841 | sensitive | 4.00 |
| AJ 12568 | resistant | 4.50 |

EXAMPLE 6 one platinum loop each of Brevibacterium flavum AJ 11841 and ATCC 12568 was scraped off from each slant and inoculated on 50 ml of seed culture medium shown in Table 8, respectively. By performing aerial spinner culture at 31.5° C. for 18 hours, the seed culture broth was prepared.

On the other hand, 300 ml of the main culture medium shown in Table 9 was separately charged in a glass-made jar fermenter of 1 liter volume and 15 ml each of the seed culture broth was inoculated thereon. Aerial spinner culture was carried out at 31.5° C. in an aerial volume of 1/1 (V/V) per minute.

While maintaining pH of the medium in the range of 7.0 to 8.0, a mixture of glucose and ammonium sulfate (mixing ratio of glucose:ammonium sulfate is 10:1; glucose concentration of the mixture is 40%) was added continuously or intermittently to the culture broth to perform fermentation at 31.5° C. for 72 hours. The results are shown in Table 10.

TABLE 8

| Composition of Seed Culture Medium | |
| --- | --- |
| Component | Concentration |
| Glucose | 15 g/l |
| Ammonium sulfate | 3 g/l |
| Urea | 1 g/l |
| $KH_2PO_4$ | 1 g/l |
| $MgSO_4.7H_2O$ | 0.4 g/l |
| $Mn^{++}$ | 2 mg/l |
| $Fe^{++}$ | 2 mg/l |
| Biotin | 50 μg/l |
| Thiamine hydrochloride | 200 μg/l |
| Soybean protein hydrolysate concentrate (total nitrogen 7%) | 30 ml/l |
| (pH 7.5) | |

TABLE 9

| Composition of Main Culture Medium | |
| --- | --- |
| Component | Concentration |
| Glucose | 10 g/l |
| Ammonium sulfate | 3 g/l |
| $KH_2PO_4$ | 1 g/l |
| $MgSO_4.7H_2O$ | 0.4 g/l |
| $Fe^{++}$ | 2 mg/l |
| $Mn^{++}$ | 2 mg/l |
| Biotin | 50 μg/l |
| Thiamine hydrochloride | 60 μg/l |
| Soybean protein hydrolysate concentrate (total nitrogen 7%) | 30 μg/l |
| (pH 7.5) | |

TABLE 10

| Strain | Sensitive or Resistant to Selys | Amount of L-Lysine HCl Accumulated (g/dl) |
| --- | --- | --- |
| ATCC 11841 | sensitive | 8.60 |
| AJ 12568 | resistant | 9.50 |

By thus culturing the Selys resistant strain in a nutrient medium, L-lysine accumulated in the culture broth markedly increases as compared to that for the parent strain. Therefore, a great reduction in cost for the production of L-lysine by fermentation occurs, in particular, on an industrial scale.

Having described the present invention, it will now be apparent to one of ordinary skill in the art that many changes and modifications can be made to the above-described embodiments without departing from the spirit or the scope of the present invention.

What is claimed as new and desired to be secured by Letters Patent of the United States is:

1. A process for producing L-lysine, which comprises culturing a mutant L-lysine-producing strain belonging to the genus Brevibacterium or the genus Corynebacterium and having selenalysine resistance in a nutrient medium containing assimilable sources of carbon, nitrogen, and inorganic salts until a sufficient amount of L-lysine is produced, and recovering said L-lysine, wherein said strain is selected from the group consisting of Brevibacterium lactofermentum AJ 12564, Corynebacterium acetoacidophylum AJ 12565, Brevibacterium lactofermentum AJ 12566, Brevibacterium flavum AJ 12568 and Corynebacterium glutamicum AJ 12579.

2. The process of claim 1, which further comprises culturing said strain in the nutrient medium at a fermentation temperature of about 30° to 35° C. for about 40 to 100 hours.

3. The process of claim 1, which further comprises maintaining the pH of said nutrient medium at about 6.5 to 7.0 .

4. The process of claim 1, wherein L-lysine is produced in an amount of at least 2.21 g/dl.

5. The process of claim 1, wherein L-lysine is produced in an amount of at least 2.31 g/dl.

6. The process of claim 1, wherein L-lysine is produced in an amount of at least 2.64 g/dl.

7. The process of claim 1, wherein L-lysine is produced in an amount of at least 2.79 g/dl.

8. The process of claim 1, wherein L-lysine is produced in an amount of at least 9.50 g/dl.

9. A mutant L-lysine-producing microorganism strain selected from the group consisting of *Brevibacterium lactofermentum* AJ 12564, *Corynebacterium acetoacidophilum* AJ 12565, *Brevibacterium lactofermentum* AJ 12566, *Brevibacterium flavum* AJ 12568 and *Corynebacterium glutamicum* AJ 12579.

* * * * *